(12) United States Patent
Nam

(10) Patent No.: US 8,435,499 B2
(45) Date of Patent: May 7, 2013

(54) TOOTHPOWDER COMPOSITION CONTAINING WHEAT FLOUR AND BAMBOO SALT

(76) Inventor: Ji-Won Nam, Uijeongbu-Si (KR)

( * ) Notice: Subject to any disclaimer, the term of this patent is extended or adjusted under 35 U.S.C. 154(b) by 691 days.

(21) Appl. No.: 12/571,285

(22) Filed: Sep. 30, 2009

(65) Prior Publication Data

US 2010/0166812 A1    Jul. 1, 2010

(30) Foreign Application Priority Data

| Dec. 30, 2008 | (KR) | .......................... 10-2008-0137229 |
| Feb. 16, 2009 | (KR) | .......................... 10-2009-0012543 |
| May 15, 2009 | (KR) | .......................... 10-2009-0042790 |
| Jul. 9, 2009 | (KR) | .......................... 10-2009-0062658 |

(51) Int. Cl.
  *A61K 8/00* (2006.01)
  *A61K 8/97* (2006.01)
  *A61K 8/022* (2006.01)
  *A61K 9/20* (2006.01)
  *A61Q 11/00* (2006.01)

(52) U.S. Cl.
  USPC ............... 424/49; 424/58; 424/401; 424/464; 424/489

(58) Field of Classification Search .................... 424/49, 424/58, 401, 464, 489
See application file for complete search history.

(56) References Cited

U.S. PATENT DOCUMENTS 6,056,944 A  *  5/2000  Finidori .......................... 424/49

FOREIGN PATENT DOCUMENTS

| CN | 1736364 | * | 2/2006 |
| JP | 05-170632 A | | 7/1993 |
| JP | 2004-300043 A | | 10/2004 |
| JP | 2007-31286 A | | 2/2007 |
| JP | 2007-527849 A | | 10/2007 |
| JP | 2008-143910 A | | 6/2008 |
| KR | 2004-0009968 | * | 1/2004 |
| KR | 10-2004-0066313 A | | 7/2004 |
| KR | 2006008509 | * | 1/2006 |
| KR | 10-0645915 B1 | | 11/2006 |

* cited by examiner

*Primary Examiner* — Lezah Roberts
(74) *Attorney, Agent, or Firm* — Knobbe Martens Olson & Bear, LLP

(57) ABSTRACT

Disclosed are a toothpowder composition and a method for manufacturing the same. The disclosed toothpowder composition contains wheat flour and bamboo salt. The method includes addition of wheat flour and bamboo salt to prepare a powder mixture. Further disclosed is a method of manufacturing a tooth-washing tablet using the toothpowder composition.

14 Claims, 2 Drawing Sheets

TOOTHPOWDER COMPOSITION CONTAINING WHEAT FLOUR AND BAMBOO SALT

This application claims priority to Korean Patent Application No. 10-2008-0137229, filed on Dec. 30, 2008, Korean Patent Application No. 10-2009-0012543, filed on Feb. 16, 2009, Korean Patent Application No. 10-2009-0042790, filed on May 15, 2009 and Korean Patent Application No. 10-2009-0062658, filed on Jul. 9, 2009 in the Korean Intellectual Property Office, the entire contents of which are hereby incorporated by reference.

BACKGROUND OF THE INVENTION

1. Field of the Invention

The present invention relates to a toothpowder composition.

2. Description of the Related Art

Toothpaste products commonly available in the market include a variety of substances. Generally, a toothpaste includes silica, calcium, magnesium, alumina, etc., as a polishing agent for mechanically cleaning teeth. However, these may cause damage on surface of a tooth dentin in a tooth crown if a particle size, hardness and/or shape of the particle is undesirable. Hence, it is necessary that a basic material of the toothpaste has a uniform particle size approximately ranging from 1 to 20 μm, a shape of the particle without sharp angles, a hardness of particle of about 3 in terms of Moss hardness.

Among ingredients of the toothpaste, a moisturizing agent may comprise glycerin, sorbitol, xylitol, glycol, etc. The toothpaste may also include fluorides (containing fluorine) for prevention of tooth cavities, a sterilizing agent containing a cationic surfactant for removing bacteria in a mouth, as well as a calculus dissolving agent that uses enzymes for inhibiting formation of plaque, sodium with a high osmotic pressure for preventing periodontal disease, and/or aminocaproic acid, allatoin, vitamins for hemostasis. Optionally, hydroxyapatite is used to fill damaged tooth dentin, to advantageously influence on sensitive teeth and to provide whitening effects. In addition, cellulose, carrageenan, gum, and the like is used as a binding agent to combine solid ingredients with liquid components. The toothpaste may further comprise an anionic surfactant containing sodium lauryl sulfate as a bubbling agent, a non-ionic surfactant comprising a copolymer of polyoxyethylene or propylene (poloxamer) as a stabilizing agent, chemical substances such as castor oil or fatty acid ester, other cleaning agents, additives such as flavor, color, a neutralizing agent, and so forth.

There are conventional technologies regarding the present invention, for example, Korean Patent Laid-Open No. 10-2004-0066313 (claiming a tooth whitening toothpaste composition containing medical herb ingredients) describes a composition including a powder or extract of medical herbs such as *Kaempferia galanga* with tooth whitening effects, pyrophosphate and fluorine. Korean Patent Laid-Open No. 10-0645915 (claiming a method for manufacturing a powdery medical herb containing toothpaste) describes a method for fabrication of a medical herb containing toothpaste in powder form, which contains 60 wt. % of salt powder and bamboo salt in a mixing ratio of 1:1, as well as talc and porphyry pulverized into powder having a particle size of 400 mesh or less.

In addition, Japanese Patent Laid-Open No. H5-170632 (claiming an oral hygienic composition with taste sense protection and mildness) describes a composition comprising dentifrice, gel, powder, mouth rinse such as protein derivatives derived from collagen, lecithin as a natural emulsifier, disodium lauryl succinate with high bubbling ability, flavor oil, anti-cariogenic fluoride, and the like. Japanese Patent Laid-Open No. 2004-300043 (claiming a chemical agent combined with bittern) describes a chemical agent for treatment of oral diseases by a percutaneous absorption method, including magnesium chloride (bittern) as a major component, which is transdermally absorbed and contains mineral ingredients often lacked in a body of a modern human in order to improve such disease conditions, and may be easily prepared at low costs. Japanese Patent Laid-Open No. 2007-31286 (claiming a tooth polishing powder and manufacturing method thereof) describes a tooth polishing powder prepared by baking shell powder at 1,100 to 1,300° C., adding the baked shell powder to an acetic acid solution to obtain a neutral calcium acetate solution with pH 6 to 8, and evaporating and drying the neutral solution to form the tooth polishing powder so as to inhibit proliferation of bacteria in a mouth. Japanese Patent Publication No. 2007-527849 (claiming an oral composition for tooth treatment based on herbal plants and a method for manufacturing the same) describes a dental composition for tooth treatment, comprising a powder or extract of herbal plants such as *Citrus karna* raf, *Zanthoxylum armatum* D.C., *Azadirachta indica* A. Juss, etc., in order to prevent tartar or tooth cavities, wherein the composition is used in various formulations such as powder (tooth polishing powder), paste, gel, dental pack, dental floss, oral rinse, chewing gum, and so forth. Japanese Patent Laid-Open No. 2008-143910 (claiming an oral composition for local use) describes an oral composition for local use, comprising at least one chemical substance selected from a group consisting of tin ion, zinc ion and copper ion, an anti-plaque agent based on polyphosphate, and an oral carrier available in medical applications. However, oral hygienic compositions or dental compositions for tooth treatment according to the above patent and/or applications in Korea and Japan are clearly distinguishable from the present invention relating to a pure medical herb based toothpowder in technical configurations thereof.

In general, a mouth refers to an oral cavity starting from lips at the front side of a face and being connected to a pharynx ending at an uvula, and has basic functions of treating food such as biting, chewing, oral digestion and/or tasting, as well as additional performances such as constructing sound of words, salivary gland endocrine behavior, breathing, and so forth. Briefly, the mouth is a first organ to receive all of nutrients absorbed by eating foods while allowing penetration of pathogens in air into the body. The mouth is mutually connected with teeth functioning to chew and speech and directly relating to aesthetic appearance, gums supporting the teeth, and a tongue contributing to actualization of a voice. Hence, the mouth significantly contributes to health of a body. Hygienic condition and health management of a mouth have been only obtained using a toothpaste comprising artificial compounds in recent years.

However, as a life span of a human is considerably extended, healthy and well-being life is becoming more important, and therefore, an interest in tooth health and oral hygiene is also increased. When foods enter into a mouth, the tongue and teeth serve to provide the taste and feel of eating, and stimulate a digestive gland to secrete digestive fluid so as to assist digestion of the food. Therefore, oral hygienic formulations based on natural substances may be more preferable than those made of chemical materials. However, consumers familiar to liquid toothpastes consisting of chemical components have currently used such liquid toothpastes without a sense of incongruity, in terms of tooth health and oral hygiene.

SUMMARY OF THE INVENTION

As an interest in healthy management of teeth is increased, conventional toothpaste products available in the market include polishing agents, binders, whitening agents, moisturizing agents and other additives, as well as medical herbal extracts or other extracts with tooth whitening effects. The toothpaste product is mostly manufactured into a liquid toothpaste in a gel state. However, major ingredients of the toothpaste for preventing tooth cavities and for removing plaque, tartar, calculus and/or oral malodor often remain in the mouth even after brushing and, when such residue accumulates on teeth, a tongue, gums and/or an oral inner wall as well as the teeth may be weakened and then cause inflammation of oral mucosa, dissecting tooth cervix, etc. Moreover, using the toothpaste gives strong stimulation to an oral cavity, leading to taste sense loss. And, even after using the toothpaste, chemical ingredients thereof still remain in the mouth while incompletely removing food residue therefrom. As a result, such toothpaste for oral management sometimes causes adverse affects to teeth and the mouth.

In consideration of conventional circumstances described above, the present inventors have researched and investigated for several years in view of high interest in health and well-being life of consumers, and consequently, invented a toothpaste composition containing natural herb ingredients in a suitable mixing ratio thereof to a base component of the composition wherein the natural ingredients have excellent performances in terms of tooth health and oral hygiene, as well as a method for manufacturing the same.

Accordingly, one aspect of the present invention provides a toothpowder composition containing wheat flour and bamboo salt.

Another aspect of the present invention provides a method for manufacturing a toothpowder composition by adding wheat flour and bamboo salt to prepare a powder mixture, and a method for manufacturing a tablet type toothpaste by applying a coating solution to the toothpowder composition prepared as described above.

The toothpowder composition of the present invention has strong anti-bacterial behavior to prevent formation of plaque, thus protecting tooth from calculus or, tongue coating deposition. The composition also exhibits cleaning and anti-inflammatory effects to remove oral malodor and different inflammations in a mouth while, simultaneously, preventing spontaneous discoloration of tooth and whitening the tooth. Using the features of the present invention can avoid processes or chemical substances harmful for a human body, instead preparing the toothpowder by simple processes such as heating, drying and pulverizing of natural herbs. The prepared toothpowder is easily dissolved in saliva inside a mouth and practically provides brushing and tooth cleaning effects by gargling only. Even if directly swallowing the toothpowder without rinsing off with water, substantially the same effects as if medical herbs are eaten may be achieved. In addition, from a result of an experiment wherein some participants swallowed the toothpowder after tooth brushing, although it is not common, it was reported that conditions of internal organs may be enhanced by the toothpowder. Moreover, it was also disclosed that, when the inventive toothpowder is used together with any conventional liquid toothpaste, the liquid toothpaste is completely decomposed not to leave a residue thereof in a gargled water.

BRIEF DESCRIPTION OF THE DRAWINGS

These and other features, aspects and advantages of the present invention will be fully described in the following detailed description of exemplary embodiments, taken in conjunction with the accompanying drawings. In the drawings.

DETAILED DESCRIPTION OF EMBODIMENTS

Figure 1:
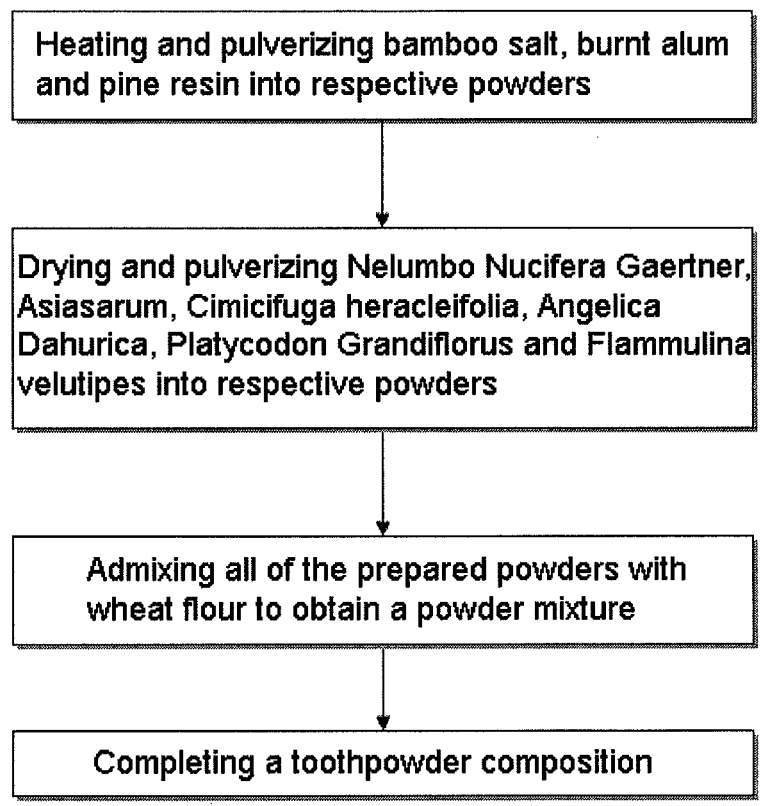
FIG. 1 is a flow chart illustrating a method for manufacturing a toothpowder composition comprising wheat flour and bamboo salt according to the present invention.
Figure 2:
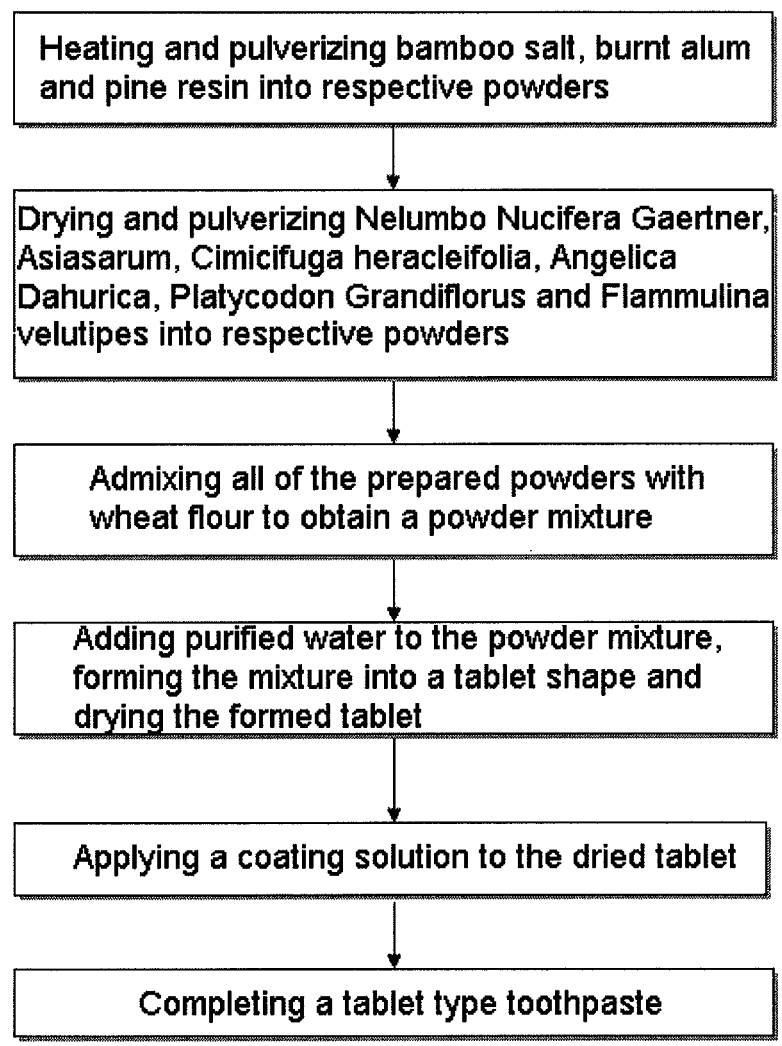
FIG. 2 is a flow chart illustrating a method for manufacturing a tablet type toothpaste by applying a coating solution to the inventive toothpowder composition.

According to an aspect of the present invention, there is provided a toothpowder composition comprising wheat flour and bamboo salt.

The toothpowder composition may comprise 20 to 40 wt. % of wheat flour and 20 to 40 wt. % of bamboo salt powder to the total weight of the composition.

Other than wheat flour and bamboo salt, the toothpowder composition of embodiments of the present invention may further comprise burnt alum and pine resin.

More particularly, the toothpowder composition of embodiments of the present invention may comprise 5 to 15 wt. % of burnt alum powder and 5 to 15 wt. % of pine resin powder to the total weight of the composition.

Other than wheat flour and bamboo salt, the inventive toothpowder composition may comprise burnt alum, pine resin, *Nelumbo Nucifera Gaertner, Asiasarum, Cimicifuga heracleifolia, Angelica Dahurica, Platycodon Grandiflorus* and *Flammulina velutipes* in extract form.

More particularly, the toothpowder composition of embodiments of the present invention may comprise 5 to 15 wt. % of burnt alum, 5 to 15 wt. % of pine resin, 2 to 6 wt. % of *Nelumbo Nucifera Gaertner*, 2 to 6 wt. % of *Asiasarum*, 2 to 6 wt. % of *Cimicifuga heracleifolia*, 2 to 6 wt. % of *Angelica Dahurica*, 1 to 3 wt. % of *Platycodon Grandiflorus* and 1 to 3 wt. % of *Flammulina velutipes* in powder form to the total weight of the composition.

According to another aspect of the present invention, there is provided a method for manufacturing a toothpowder composition which comprises adding wheat flour and bamboo salt to prepare a powder mixture.

For the above preparation method, the powder mixture may further comprise burnt alum, pine resin, *Nelumbo Nucifera Gaertner, Asiasarum, Cimicifuga heracleifolia, Angelica Dahurica, Platycodon Grandiflorus* and *Flammulina velutipes* in extract form as well as wheat flour and bamboo salt.

The inventive method for manufacturing a toothpowder composition may comprise: heating and pulverizing bamboo salt, burnt alum and pine resin to prepare respective powders, while drying each of *Nelumbo Nucifera Gaertner, Asiasarum, Cimicifuga heracleifolia, Angelica Dahurica, Platycodon Grandiflorus* and *Flammulina velutipes* and pulverizing the dried materials into powders; and admixing all of the prepared powders together with wheat flour to obtain a powder mixture.

In the method for manufacturing the toothpowder composition, each of the powders is obtained by pulverizing all of materials into powders with desired sizes, such as bamboo salt having 0.1 to 150 μm, burnt alum having 0.1 to 3 μm, pine resin having 0.1 to 50 µm, *Nelumbo Nucifera Gaertner* having 0.1 to 55 µm, *Asiasarum* having 0.1 to 10 µm, *Cimicifuga heracleifolia* having 0.1 to 10 µm, *Angelica Dahurica* having 0.1 to 25 µm, *Platycodon Grandiflorus* having 0.1 to 70 µm, *Flammulina velutipes* having 0.1 to 80 µm and wheat flour having 0.1 to 25 µm, so as to be screened through a sieve having 150 to 180 mesh.

According to another aspect of the present invention, there is provided a method for manufacturing a tablet type toothpaste which comprise applying a coating solution to the toothpowder composition prepared as described above.

The method for manufacturing the tablet type toothpaste may comprise: adding purified water to the toothpowder composition of embodiments of the present invention, forming the mixture into a tablet shape and drying the formed tablet; and applying a coating solution containing hydroxypropyl methylcellulose to the dried tablet.

Alternatively, the inventive method for manufacturing the tablet type toothpaste may comprise: adding purified water to the toothpowder composition of embodiments of the present invention, forming the mixture into a tablet shape and drying the formed tablet; and applying a coating solution containing palatinose to the dried tablet.

Hereinafter, the toothpowder composition containing wheat flour and bamboo salt, the method for manufacturing the toothpowder composition by adding wheat flour and bamboo salt to obtain a powder mixture, and the method for manufacturing a tablet type toothpaste by applying a coating solution to the toothpowder composition prepared as described above according to embodiments of the present invention will be described in greater detail.

The present invention provides a toothpowder composition comprising wheat flour and bamboo salt. Other than wheat flour and bamboo salt, the toothpowder composition may further comprise burnt alum and pine resin. Alternatively, the toothpowder composition may comprise burnt alum, pine resin, *Nelumbo Nucifera Gaertner, Asiasarum, Cimicifuga heracleifolia, Angelica Dahurica, Platycodon Grandiflorus* and *Flammulina velutipes* in addition to wheat flour and bamboo salt.

Preferably, the inventive toothpowder composition comprises 20 to 40 wt. % of wheat flour, 20 to 40 wt. % of bamboo salt powder, as well as 5 to 15 wt. % of burnt alum, 5 to 15 wt. % of pine resin in powder form to the total weight of the composition. Preferably, other than wheat flour and bamboo salt powder, the inventive toothpowder composition also comprises 5 to 15 wt. % of burnt alum, 5 to 15 wt. % of pine resin, 2 to 6 wt. % of *Nelumbo Nucifera Gaertner,* 2 to 6 wt. % of *Asiasarum,* 2 to 6 wt. % of *Cimicifuga heracleifolia,* 2 to 6 wt. % of *Angelica Dahurica,* 1 to 3 wt. % of *Platycodon Grandiflorus* and 1 to 3 wt. % of *Flammulina velutipes* in powder form to the total weight of the composition.

More preferably, the inventive toothpowder composition comprises 30 wt. % of wheat flour, 30 wt. % of bamboo salt powder, as well as 10 wt. % of burnt alum, 10 wt. % of pine resin, 4 wt. % of *Nelumbo Nucifera Gaertner,* 4 wt. % of *Asiasarum,* 4 wt. % of *Cimicifuga heracleifolia,* 4 wt. % of *Angelica Dahurica,* 2 wt. % of *Platycodon Grandiflorus* and 2 wt. % of *Flammulina velutipes* in powder form to the total weight of the composition.

As mentioned above, the toothpowder composition of an embodiment includes the foregoing natural medical herbs or edible substances and, among those, bamboo salt and burnt alum as mineral substances are pulverized powders obtained by heating each of the substances at a high temperature, then, solidifying and pulverizing the heated materials. As a crop based food material, wheat flour is prepared by pulverizing an organic wheat harvested and well-dried with a water content of not more than 14%, and screening the powder through a sieve having 150 to 180 mesh. The natural pine resin is obtained by heating the resin at a high temperature, purifying, solidifying and pulverizing the purified material to produce the pine resin powder. In addition, each of other six herbal plants, that is, *Nelumbo Nucifera Gaertner, Asiasarum, Cimicifuga heracleifolia, Angelica Dahurica, Platycodon Grandiflorus* and *Flammulina velutipes* is dried under shade, pulverized while maintaining a water content of not more than 12%, and screened through a sieve having 150 to 180 mesh, thus resulting in a desired powder.

The present invention also discloses a method for manufacturing a toothpowder composition by adding wheat flour and bamboo salt to obtain a powder mixture. This method may comprise: heating and pulverizing bamboo salt, burnt alum and pine resin to prepare respective powders, while drying each of *Nelumbo Nucifera Gaertner, Asiasarum, Cimicifuga heracleifolia, Angelica Dahurica, Platycodon Grandiflorus* and *Flammulina velutipes* and pulverizing the dried materials into powders; and admixing all of the prepared powders together with wheat flour to obtain a powder mixture.

Preferably, the powder mixture includes bamboo salt having 0.1 to 150 µm, burnt alum having 0.1 to 3 µm, pine resin having 0.1 to 50 µm, *Nelumbo Nucifera Gaertner* having 0.1 to 55 µm, *Asiasarum* having 0.1 to 10 µm, *Cimicifuga heracleifolia* having 0.1 to 10 µm, *Angelica Dahurica* having 0.1 to 25 µm, *Platycodon Grandiflorus* having 0.1 to 70 µm, *Flammulina velutipes* having 0.1 to 80 µm and wheat flour having 0.1 to 25 µm in powder form.

More preferably, the powder mixture includes bamboo salt having 5 to 20 µm, burnt alum having 0.5 to 1.0 µm, pine resin having 1 to 10 µm, *Nelumbo Nucifera Gaertner* having 1 to 10 µm, *Asiasarum* having 0.5 to 1 µm, *Cimicifuga heracleifolia* having 0.5 to 1 µm, *Angelica Dahurica* having 0.5 to 1 µm, *Platycodon Grandiflorus* having 1 to 10 µm, *Flammulina velutipes* having 1 to 10 µm and wheat flour having 5 to 20 µm in powder form.

The following description for each of the prepared 10 materials will be given of a preparation method and functional effects thereof in an oral cavity and/or a body of a human.

(1) Wheat flour is prepared by finely pulverizing domestic wheat which was organically harvested (manufactured by Dong-A flour mills Co. Ltd.). Well-dried organic wheat having a water content of not more than 14% was pulverized and screened through a sieve having 150 to 180 mesh to obtain a fine powder. The fine powder may be used in an amount of 20 to 40 wt. %, preferably 30 wt. % to the total weight of the composition. The wheat flour may have a particle size of 0.1 to 25 µm, preferably, 5 to 20 µm. Since the wheat flour is warm and sweet and, when eating, may reinforce the stomach and the bowels and enhance stamina or energy, thus assisting behavior of internal organs. According to Dong Ui Bo Gam (as a traditional Korean medical handbook), the wheat flour has been used to treat tetanus, jaundice and/or mumps, to reinforce immune performance and to prevent ageing, and exhibited excellent degradation of bad cells. Moreover, the wheat flour is easily dissolved in a mouth and shows superior cleaning effects to remove impurities. Hence, for modern people having preferences to meat, animal fats remained in the mouth and residues in the internal organs may be considerably removed. Moreover, the wheat flour may also function as an emulsifying agent to prevent damage to tooth dentins caused by tooth brushing and exhibit excellent whitening effects.

(2) Bamboo salt is a processed salt (treated by a traditional medical process) obtained by means of a traditional bamboo extraction using a bamboo barrel wherein salt was baked one to nine times at 1,300 to 2,000° C. to remove toxic materials harmful to a human body. Briefly, according to an embodiment of the present invention, natural sun-dried salt (produced at the west sea of Korea) containing plenty of minerals was filled in an amount of 7 to 8 parts by volume in a live bamboo barrel grown for 3 to 5 years and the salt filled bamboo barrel was sealed using loess soil, followed by repeatedly baking eight (8) times at 800° C. using pine firewood. After baking 8 times, the treated bamboo barrel was lastly heated to more than 1,300° C. by injecting pine resin over the pine firewood. Here, the salt was completely fused and flowed in a gel state. Moisture of the bamboo barrel, that is, bamboo water was combined with the fused salt as well as sulfur in the loess soil used for sealing the barrel to form a liquid mixture. The liquid mixture was cooled overnight, resulting in a hard stone-like solid. The resulting solid is known as bamboo salt. Such bamboo salt may comprise any conventional processed salt products with reliability commercially available in the market. Pulverizing and screening the bamboo salt may obtain a powder having 150 to 180 mesh scale. The bamboo salt may be used in an amount of 20 to 40 wt. %, preferably 30 wt. % to a total weight of the toothpowder composition. A particle size of the bamboo salt may range from 0.1 to 150 μm, preferably 5 to 20 μm (Analysis of particle sizes was performed using a FE-SEM apparatus). The processed bamboo salt powder free from different impurities contained in natural sun-dried salt is salty, but the salty taste is rapidly removed in the mouth while leaving a good (sweet) taste. The bamboo salt powder also contains various beneficial ingredients. The bamboo salt has excellent medical effects to periodontal diseases and, especially, to tonsillitis and esophageal stomatitis. Instead of tooth brushing, gargling only may attain such advantageous effects. Moreover, it was recorded that the bamboo salt prevents tooth cavities and periodontitis, is effective to treat tooth pain and/or oral inflammation and, when taken with a tangleweed infusion in water, may detoxify nicotine in the body. As for the bamboo salt, bamboo, sulfur crystals, pine resin, and a soil fraction and/or an iron ingredient in loess as well as salt promoting body metabolism are combined under flame heat during processing, so as to induce a synergy effect mechanism of negative positive five elements (metal, wood, water, fire and earth), thus considerably reinforcing blood cleaning and anti-inflammatory activities. Hence, the bamboo salt is a healthy salt widely used in related applications including, for example, anyone independent of body characteristics and/or a variety of diseases. The bamboo salt may convert acidic foods into alkaline ones and provide minerals beneficial to the human body, thereby increasingly attracting attention as a useful healthy food additive for modern humans suffering from pollution.

(3) Burnt alum is obtained by baking an alum to eliminate crystalline water from the alum. The burnt alum in a powder form has reduced solubility in water and is slowly dissolved to form a substantially transparent solution. A process of preparing the burnt alum comprises first heating an alum to more than 120° C. to boil it and form an expanded alum in a liquid state, and chilling the liquid alum to room temperature so as to obtain a hard solid product. Pulverizing the solid product and screening the powder through a sieve with 150 to 180 mesh resulted in a fine and milk white powder such as wheat flour. The burnt alum may used in an amount of 5 to 15 wt. %, preferably 10 wt. % to the total weight of the composition. A particle size of the burnt alum may range from 0.1 to 3 μm, preferably 0.5 to 1 μm. The burnt alum has an inherent sour taste effective to inhibit bacteria, preservative effects and excellent anti-inflammatory effects in a mouth such as toward gums, a tongue and/or roof of an oral cavity. Hence, inflammation in a mouth-respiratory system such as sore throat, tonsillitis, laryngitis, etc. may be prevented. In particular, when effective ingredients of the toothpowder composition according to an embodiment are combined with pine resin, these may be suitably adhered to respective parts in the oral cavity to reinforce gums, thereby strengthening and improving teeth while efficiently preventing periodontitis.

(4) Pine resin is a liquid obtained from a pine wood, which is transparent and colorless soon after extracting while being translucent and sticky with a lapse of time, thus leading to precipitation of a white solid from resin acid. After naturally hardening the pine resin, the resin was boiled in water containing ashes of Mulberry tree (ash solution) or ethyl alcohol (spirit) and was immersed in cold water. This process was repeated until impurities in the pine resin are completely removed while a pine sap having a transparent brown core like a Yeot (Korean traditional candy based on crop plants) is solidified and obtained. Such solidified pine resin was entered into a stainless steel container, followed by heating at a high temperature so as to evaporate moisture present therein and generate a more transparent liquid with gardenia yellow color. After cooling the pine resin liquid, the obtained product was pulverized and screened through a sieve having 150 to 180 mesh to produce the pine resin powder.

The pine resin powder may be used in an amount of 5 to 15 wt. %, preferably 10 wt. % to the total weight of the toothpowder composition. A particle size of the pine resin powder may range from 0.1 to 50 μm, preferably 1 to 10 μm. Pine resin is warm, sweet and bitter, non-toxic, decreases heat while relaxing internal organs, recovers gum skin, has analgesic and anti-inflammatory effects. Because of anti-inflammatory effects, the pine resin may efficiently prevent and treat tooth cavities and exhibit excellent anti-bacterial properties. Hence, the pine resin may function to remove various harmful bacteria present in the gums and/or tongue as well as plaque or calculus between teeth and tongue coating.

(5) *Nelumbo Nucifera Gaertner* is obtained by taking seeds of lotus, removing skin of the seeds, drying the seeds under shade to have a water content of not more than 15%, pulverizing the dried seeds and screening the powder through a sieve having 150 to 180 mesh to obtain the product with desired particle size. *Nelumbo Nucifera Gaertner* may be used in an amount of 2 to 6 wt. %, preferably 4 wt. % to the total weight of the composition. A particle size of the obtained powder may range from 0.1 to 55 μm, preferably 1 to 10 μm. This herbal plant is warm, sweet and astringent, supports blood circulation, energy and internal organs, reinforces activity of the heart, and helps the body and mind relax. Also, *Nelumbo Nucifera Gaertner* contains plenty of minerals such as calcium, phosphorus, iron, potassium, etc. and vitamin B1, so as to provide effective nutrients into the mouth. Lecithin contained in *Nelumbo Nucifera Gaertner* regenerates damaged liver cells and improves cholesterol levels, supplies nutrients to a brain, and performs anti-oxidation and enhanced blood circulation. In addition, thanks to high emulsion ability to combine oil with water, this herbal plant can efficiently remove animal fats accumulated in blood vessels or the oral cavity. Hence, fine waste or residue in the mouth may be effectively eliminated and the tooth ridge and the tongue may be cleanly maintained. Moreover, a smooth blood circulation may be accomplished so as to healthily manage various tissues in the oral cavity. Especially, the salivary gland is stimulated to secrete salvia and to prevent the oral cavity from being dried during tooth brushing, has excellent cleansing effects so that the salvia becomes clear and is combined with other different compositions so as to remove tongue coating and oral malodor after using *Nelumbo Nucifera Gaertner*.

(6) *Asiasarum* is obtained by washing roots and stalks of *Asiasarum heterotropoides* F. Maekawa var. *mandshuricum* F. Maekawa and/or *Asiasarum sieboldi* F. Maekawa, drying the herbal plant under shade to have a water content of not more than 15%, pulverizing the dried herbal plant and screening the pulverized material through a sieve having 150 to 180 mesh to obtain a powder with a desired particle size. The powder may be used in an amount of 2 to 6 wt. %, preferably 4 wt. % to the total weight of the composition and a particle size of the powder may range from 0.1 to 10 μm, preferably 0.5 to 1 μm. *Asiasarum* is warm, spicy and non-toxic, is mostly used to treat pathogenic wind-moisture related pain and to warm internal organs and stabilize internal energy, efficiently alleviates nasal congestion and sore throat diseases. This product may enhance bladder functions, treat headache or head skin inflammatory diseases, and improve eyesight of a human. The *Asiasarum* powder may also reduce phlegm and may be used as a diaphoretic material. Toothache due to pathogenic wind-chill conditions and/or decayed tooth may be treated and gingival inflammation may be efficiently reduced. Moreover, the *Asiasarum* powder may remove oral malodor and take care of teeth to be more clean and polished.

(7) *Cimicifuga heracleifolia* is a root of a perennial plant from Ranunculaceae, Ranales among dicotyledonous plants. This herbal plant is extracted, washed, dried under shade to have a water content of not more than 15%. The treated plant is pulverized and screened through a sieve having 150 to 180 mesh to obtain a powder with a desired particle size. The obtained powder may be used in an amount of 2 to 6 wt. %, preferably 4 wt. % to the total weight of the composition. A particle size of the powder may range from 0.1 to 10 μm, preferably 0.5 to 1 μm. *Cimicifuga heracleifolia* has sweet properties and bitter taste, but, is not toxic. Hence, this herbal plant is directly used to treat inflammatory diseases in the oral cavity due to bacterial infection and, when combined with the bamboo salt, synergic effects may be obtained. In addition, swollen tooth ridge or severe toothache caused by periodontal diseases, gingival bleeding due to a loose molar tooth or tooth root, etc. may be efficiently cured. According to Dong Ui Bo Gam, it is described that *Cimicifuga heracleifolia* detoxifies numerous kinds of poisons, improves stamina, energy, vitality and/or sperm generation, and removes body wastes, thus efficiently treating injury of the throat and inflammation in the mouth.

(8) *Angelica Dahurica* refers to a root of *Angelica Dahurica*. This herbal plant is washed and dried under shade to have a water content of not more than 15%. After pulverizing the prepared herbal plant, the pulverized material is screened through a sieve having 150 to 180 mesh to obtain a powder with a desired particle size. The obtained powder may be used in an amount of 2 to 6 wt. %, preferably 2 wt. % to the total weight of the composition. A particle size of the powder may range from 0.1 to 25 μm, preferably 0.5 to 1 μm. *Angelica Dahurica* is warm, spicy and non-toxic, and is effectively used to treat pathogenic wind-heat conditions (that is, various symptoms caused by heat such as fever, chill, yellow tongue coating, etc.) and pathogenic wind-dizziness (that is, cold caused dizziness, stiff neck, etc.). Also, discoloration on face may be eliminated and anti-bacterial and/or anti-inflammatory effects may be expected. Moreover, the above herbal plant may remove abscess of gums and, especially, may efficiently treat inflammation of a molar tooth. *Angelica Dahurica* also has tooth whitening effects so as to clean and polish teeth.

(9) *Platycodon Grandiflorus* is named bellflower and refers to the root of a broad bellflower. The root is dried in the air to have a water content of not more than 15%, being hardened like a dried ginseng root. After pulverizing the root, the pulverized material is screened through a sieve having 150 to 180 mesh to obtain a powder with desired particle size. The powder may be used in an amount of 1 to 3 wt. %, preferably 2 wt. % to the total weight of the composition and a particle size of the powder may range from 0.1 to 70 μm, preferably 1 to 10 μm. *Platycodon Grandiflorus* is slightly warm, spicy and bitter. This herbal plant may clean a lung, alleviate tightness in chest or chest heating, and warm chilled bowels. *Platycodon Grandiflorus* comprises saponine as a major ingredient, which is well known to have a variety of pharmacological efficacies. According to Dong Ui Bo Gam, it is described that this herbal plant is used as a medicine for tonsillitis, abdominal pain, hemostasis, dry cough, expectoration, asthma, pharyngitis, and so forth.

(10) *Flammulina velutipes* refers to a white mushroom from tricholomataceae, Agaricales, Basidiomycetes. The white mushroom is washed using water and dried under shade for about one month to obtain a dried material like a brown fallen leaf. After drying again the brown material to have a water content of not more than 150, the dried material is pulverized and screened through a sieve having 150 to 180 mesh to obtain a powder with a desired particle size. *Flammulina velutipes* powder is prepared by a simple process, and conventional products available in the market may be used. The above mushroom powder may be used in an amount of to 3 wt. %, preferably 2 wt. % to the total weight of the composition and a particle size of the powder may range from 0.1 to 80 μm, preferably 5 to 20 μm. *Flammulina velutipes* is warm and may be used to reduce blood cholesterol, support a liver and treat stomach diseases. In particular, a white stalk portion thereof may improve functions of a respiratory system, have high protein and low calories and contain plenty of natural vitamins to accelerate growth of bones and teeth. Hence, *Flammulina velutipes* may be an excellent food for growing children. Guanylic acid contained in *Flammulina velutipes* is well known to decrease a cholesterol level and enhance blood circulation, exhibiting superior medical efficacies to atherosclerosis, heart disease, hyperlipidemia, etc. In addition, the above mushroom may stimulate an immune system to protect a human body from different viral infections which in turn inhibits cancer generation. This mushroom also includes other components beneficial to brain development. Dietary fibers abundant in the mushroom may clean a surface of teeth to prevent calculus, while enokipodins with anti-bacterial activity inhibits growth of *s. mutans* causing tooth cavities, thus efficiently preventing tooth cavities. Moreover, discoloration of teeth caused by green tea or coffee may be prevented.

As described above, such materials have five (5) respective tastes (acidic, bitter, sweet, spicy, astringent) and a combination of these tastes may derive synergic effects, leading to a unique taste.

Medical efficacies and/or effects of each of the above substances are in traditional Korean medical handbooks such as Bon Cho Gang Mok and Dong Ui Bo Gam, as well as other traditional handbooks relating to oriental herbal plants, the entire contents of which are incorporated herein by reference. The present invention provides a new toothpowder composition with improved performance using a unique combination of medical herb formulations as described above. The above described process for preparation of respective traditional medical herbs is an exemplary embodiment and a person skilled in the art will appreciate that modifications and/or variations thereof can be made without deterioration of inherent efficacies of herbal plants in the medicine.

The present invention provides a method for manufacturing a tablet type toothpaste which comprise applying a coating solution to the toothpowder composition prepared according to embodiments of the present invention. This method may comprise: adding purified water to the toothpowder composition, forming the mixture into a tablet shape and drying the formed tablet; and applying a coating solution containing hydroxypropyl methylcellulose or palatinose to the dried tablet.

Preferably, the inventive method for manufacturing the tablet type toothpaste comprises: adding 10 to 30 wt. parts of purified water to 100 wt. parts of toothpowder composition, kneading the mixture, forming the mixture into a tablet shape having a diameter of 1 to 5 mm and drying the tablet; and applying a coating solution containing 0.1 to 10 wt. % of hydroxypropyl methylcellulose or palatinose and 0.1 to 10 wt. % of xylitol to the tablet by a spray gun.

More preferably, the method for manufacturing the tablet type toothpaste comprises: adding 15 to 25 wt. parts of purified water to 100 wt. parts of toothpowder composition, kneading the mixture, forming the mixture into a tablet shape having a diameter of 2 to 4 mm and drying the tablet; and applying a coating solution containing 0.5 to 1 wt. % of hydroxylpropyl methylcellulose or palatinose and 0.5 to 1 wt. % of xylitol to the tablet by a spray gun.

One tablet of the toothpaste may have a weight of 140 to 160 mg and a tablet type toothpaste product may be manufactured by press through pack (PTP).

Such a tablet type toothpaste may be a disposable product with convenient carrying and use. Fabrication of such a tablet type toothpaste may enable more convenient and easy management of teeth and oral conditions by a user familiar with fast food culture in his busy life.

Hydroxypropyl methylcellulose (HPMC) is a well-known food additive to increase adhesiveness and viscosity of food, improve emulsion stability, and enhance physical properties and texture. HPMC is an odorless yellowish white fibrous powder or granule, and is generally used as an emulsifier, stabilizer or thickener. This substance produces a viscous suspension like a transparent opal when swollen in water, however, is not dissolved in alcohol. This substance has moisture absorption and pH 5.0 to 8.0 is varied into a sol or a gel by heating and cooling. An acceptable daily intake (ADI) of HPMC is not particularly restricted, however, a $LD_{50}$ dose of 5,200 mg/kg of HPMC was administrated to a rat by intraperitoneal injection. In addition to common use of HPMC as an emulsifier, stabilizer or thickener for foods, this compound may optionally serve as a dispersant for preparation of bread, ice cream, salad, and the like.

The other compound described above, that is, palatinose is also well-known to have favorable sweet taste, to prevent tooth cavities or diabetes and to function as a well-being sugar. Although palatinose still is referred to as 'natural sugar', 'sugar without causing tooth cavities', or 'sugar enhancing brain performance', etc., clinical experiments performed in Brazil and other countries demonstrated that the above compound is substantially ideal for embodying low glycemic index products (G.I., blood sugar index). Palatinose contained in sugar canes or honey is obtained by enzyme treatment of sugar, wherein the above compound is desirably sweet and stable such as sugar and supplies optimal energy to the brain.

However, unlike the sugar, palatinose is not easily used by microorganisms or enzymes, thus not causing tooth cavities. Moreover, a blood sugar level is not decreased due to insulin and hypertension after eating foods, thus preventing geriatric diseases such as diabetes, obesity, etc. In particular, G.I. of palatinose may be about 44, which is considerably less than that of other sugar, for example, glucose, sucrose, liquid fructose, etc. The major reason of such facts is expected that in vivo decomposition and/or absorption rate of palatinose is very slow, compared to other sugars. Palatinose has an inherently low G.I and, if combined with any sugar having high G.I. or carbohydrate, palatinose serves to delay a metabolic rate of the sugar or carbohydrate which in turn decreases G.I. of the combination. Moreover, in view of physical properties, palatinose is often employed in manufacture of soft candy or jelly, in order to prevent the soft candy or jelly from adhering to teeth.

Hereinafter, the present invention will be described in greater detail by the following examples and experimental examples. However, these examples are given for illustrative purposes and not intended to limit the scope of the present invention.

First, a detailed description for examples of the present invention will be given.

EXAMPLES

Example 1

Preparation of Toothpowder Composition

1. Preparation of Bamboo Salt, Burnt Alum and Pine Resin Powders

Bamboo salt, burnt alum and pine resin purchased in the market were heated and solidified respectively. Each of the prepared materials was pulverized into powder using a typical grinding device. Alternatively, processed powder products thereof may be commercially available in the market.

2. Preparation of *Nelumbo Nucifera Gaertner, Asiasarum, Cimicifuga heracleifolia, Angelica Dahurica, Platycodon Grandiflorus* and *Flammulina velutipes* in Powder Form

*Nelumbo Nucifera Gaertner, Asiasarum, Cimicifuga heracleifolia, Angelica Dahurica, Platycodon Grandiflorus* and *Flammulina velutipes* purchased in the market were dried under shade respectively. Each of the prepared materials was pulverized into powder using a typical grinding device. Alternatively, processed powder products thereof may be commercially available in the market.

3. Combination of the Prepared Powders with Wheat Flour

The powders prepared in the foregoing No. 1 and No. 2 were fully blended with wheat flour to obtain a toothpowder composition (100 wt. %). In terms of a content by weight of the powder, the toothpowder composition comprises: wheat flour 0.3 kg (30 wt. %); bamboo salt powder 0.3 kg (30 wt. %); burnt alum powder 0.1 kg (10 wt. %); pine resin powder 0.1 kg (10 wt. %); *Nelumbo Nucifera Gaertner* powder 0.04 kg (4 wt. %); *Asiasarum* powder 0.04 kg (4 wt. %); *Cimicifuga heracleifolia* powder 0.04 kg (4 wt. %); *Angelica Dahurica* powder 0.04 kg (4 wt. %); *Platycodon Grandiflorus* powder 0.02 kg (2 wt. %); and *Flammulina velutipes* powder 0.02 kg (2 wt. %).

Examples 2 to 7

Preparation of Toothpowder Composition

The same procedures in Example 1 were repeated to prepare toothpowder compositions except that wheat flour, bamboo salt powder, burnt alum powder and pine resin powder with different contents thereof were used (see Table 1).

TABLE 1

(unit: kg)

|  | Wheat flour | Bamboo salt powder | Burnt alum powder | Pine resin powder | Note |
|---|---|---|---|---|---|
| Example 2 | 0.7 | 0.3 | 0 | 0 | Except the |
| Example 3 | 0.5 | 0.5 | 0 | 0 | others (*Nelumbo* |
| Example 4 | 0.3 | 0.7 | 0 | 0 | *Nucifera* |
| Example 5 | 0.4 | 0.4 | 0.2 | 0 | Gaertner, |
| Example 6 | 0.4 | 0.4 | 0 | 0.2 | *Asiasarum*, |
| Example 7 | 0.4 | 0.4 | 0.1 | 0.1 | etc.) |

Comparative Example 1

Preparation of Toothpowder Composition without Wheat Flour

The same procedures in Example 7 were repeated to prepare a toothpowder composition except that wheat flour was not added.

Comparative Example 2

Preparation of Toothpowder Composition without Bamboo Salt Powder

The same procedures in Example 7 were repeated to prepare a toothpowder composition except that bamboo salt powder was not added.

Examples 8 to 16

Preparation of Toothpowder Composition

The same procedures in Example 1 were repeated to prepare toothpowder compositions except that *Nelumbo Nucifera Gaertner, Asiasarum, Cimicifuga heracleifolia, Angelica Dahurica, Platycodon Grandiflorus* and *Flammulina velutipes* powders with different contents thereof were added (see Table 2).

Example 17

Manufacture of Tablet Type Toothpaste Using Toothpowder Composition

1. Tablet Forming and Drying

To the toothpowder composition prepared according to Example 1, 0.2 kg of purified water was added. After fully kneading the mixture, a tablet having a diameter of 3 mm was formed. The formed tablet was dried using a warm air dryer.

2. Coating of the Dried Tablet

Using a spray gun, a coating solution containing hydroxypropyl methylcellulose and xylitol in an amount of 0.7 wt. %, respectively, was sprayed over the dried tablet obtained from the foregoing No. 1. Drying the coated tablet resulted in a tablet type toothpaste. One tablet of the toothpaste had a weight of 140 to 160 mg.

Example 18

Manufacture of Tablet Type Toothpaste Using Toothpowder Composition

1. Tablet Forming and Drying

After adding 0.2 kg of purified water to the toothpowder composition prepared according to Example 1 and fully kneading the mixture, the obtained mixture was formed into a tablet having a diameter of 3 mm. The formed tablet was dried using a warm air dryer.

2. Coating of the Dried Tablet

Using a spray gun, a coating solution containing palatinose and xylitol in an amount of 0.7 wt. %, respectively, was sprayed over the dried tablet obtained from the foregoing No. 1. Drying the coated tablet resulted in a tablet type toothpaste. One tablet of the toothpaste had a weight of 140 to 160 mg.

Hereinafter, experimental examples for the toothpowder compositions and the tablet type toothpastes prepared according to the foregoing examples and comparative examples will be described in greater detail.

TABLE 2

(unit: kg)

|  | *Nelumbo Nucifera Gaertner* powder | *Asiasarum* powder | *Cimicifuga heracleifolia* powder | *Angelica Dahurica* powder | *Platycodon Grandiflorus* powder | *Flammulina velutipes* powder | Note |
|---|---|---|---|---|---|---|---|
| Example 8 | 0 | 0.04 | 0.04 | 0.04 | 0.01 | 0.01 | *1 |
| Example 9 | 0.04 | 0 | 0.04 | 0.04 | 0.01 | 0.01 | |
| Example 10 | 0.04 | 0.04 | 0 | 0.04 | 0.01 | 0.01 | |
| Example 11 | 0.04 | 0.04 | 0.04 | 0 | 0.01 | 0.01 | |
| Example 12 | 0.04 | 0.04 | 0.04 | 0.04 | 0 | 0.01 | |
| Example 13 | 0.04 | 0.04 | 0.04 | 0.04 | 0.01 | 0 | |
| Example 14 | 0 | 0 | 0.04 | 0.04 | 0.01 | 0.01 | |
| Example 15 | 0 | 0 | 0 | 0.04 | 0.01 | 0.01 | |
| Example 16 | 0 | 0 | 0 | 0 | 0.01 | 0.01 | |

*1: Each of Wheat flour and bamboo salt powder, 0.3/Each of burnt alum and pine resin, 0.1

Experimental Example 1

Experiment for Properties of Prepared Powders

1. Measuring Water Content of Each of the Prepared Powders

A water content of each of powders prepared in the inventive method was measured. For 10 materials (dried powders) obtained in Example 1, analysis for water contents thereof was requested to Korea Food Research Institute by reference on 13 Jan., 2009 (with File No. AO 2009-01-13-010), and test results of such analysis are shown in the following Table 3.

TABLE 3

Measured results of water contents in materials (unit: %)

| Sample | Water content | Unit | Test method |
| --- | --- | --- | --- |
| Pine resin | 1.2 | g/100 g | Food Code |
| *Flammulina velutipes* | 8.2 | g/100 g | (2008), heating and drying at |
| Wheat flour | 10.8 | g/100 g | atmospheric |
| *Cimicifuga heracleifolia* | 3.9 | g/100 g | pressure |
| *Platycodon Grandiflorus* | 5.4 | g/100 g | |
| *Asiasarum* | 8.2 | g/100 g | |
| Bamboo salt | 0.2 | g/100 g | |
| *Nelumbo Nucifera* Gaertner | 8.9 | g/100 g | |
| Burnt alum | 0.9 | g/100 g | |
| *Angelica Dahurica* | 6.3 | g/100 g | |

2. Measuring Particle Size of Each of Prepared Powders

After screening each of the powders dried and pulverized according to Example 1 through a sieve having 150 to 180 mesh, the screened powder was subjected to measurement of a particle size. In order to analyze the particle size, a device FE-SEM was used (see Table 4).

TABLE 4

Measured results of particle sizes of powders (unit: μm)

| Sample | Particle size |
| --- | --- |
| Pine resin | 1 to 10 |
| *Flammulina velutipes* | 1 to 10 |
| Wheat flour | 5 to 20 |
| *Cimicifuga heracleifolia* | 0.5 to 1 |
| *Platycodon Grandiflorus* | 1 to 10 |
| *Asiasarum* | 0.5 to 1 |
| Bamboo salt | 5 to 20 |
| *Nelumbo Nucifera* Gaertner | 1 to 10 |
| Burnt alum | 0.5 to 1 |
| *Angelica Dahurica* | 0.5 to 1 |

Experimental Example 2

Determination of Tooth Whitening Effect

1. Measurement Procedure

In order to compare tooth whitening effects between toothpowder compositions in Examples 1 to 16 and Comparative Examples 1 and 2, the following measurement was performed. Also, commercial available toothpastes such as 'Song-yeom chi yak' (referring to a pine salt toothpaste, manufactured by Amore Pacific Corp.; Control 1), 'Juk-yeom chi yak' (referring to a bamboo salt toothpaste, manufactured by LG Household & Health Care Ltd.; Control 2) were used as controls for purposes of comparing tooth whitening effects thereof with embodiments of the present invention.

First of all, cigarette material, coffee, black tea, sugar and calcium were mixed to prepare a gel material. The gel was placed in a user container fixed on a rotation plate of a rotator. A tooth extracted from a healthy human aged 20 to 30 years was prepared as a specimen by exposing a surface of the tooth with a size of 2 mm (width)×2 mm (length) while coating the other part thereof with epoxy resin. The tooth specimen was fixed in the user container using epoxy resin. While rotating the user container having the specimen for 3 days, spots adhered to the specimen were dried. Here, in order to accelerate drying of the spots, an incandescent light was mounted in a upper center part of the rotation plate. Next, the specimen having the spots was subjected to brightness measurement using a colorimeter SZ (manufactured by Nippon Denshoku). Then, after mounting the specimen on a reciprocation type polishing measurement device, a soft tooth brush was fixed to a movable axis in order to rub the brush against the specimen. 0.5 g of each of the compositions (specimens) obtained in Examples and Comparative Examples was placed on a tip of the tooth brush, followed by reciprocating the tooth brush 180 times per minute. The treated specimen was subjected to color difference measurement and degree of improvement in brightness was converted into a percentage unit (%).

2. Test Results

TABLE 5

Measured results of tooth whitening effects
(unit: improvement rate of whiteness %)

| | Improvement rate of whiteness |
| --- | --- |
| Toothpowder composition prepared in Example 1 | 135.4 |
| Toothpowder composition prepared in Example 2 | 117.9 |
| Toothpowder composition prepared in Example 3 | 118.2 |
| Toothpowder composition prepared in Example 4 | 116.3 |
| Toothpowder composition prepared in Example 5 | 120.4 |
| Toothpowder composition prepared in Example 6 | 121.6 |
| Toothpowder composition prepared in Example 7 | 127.6 |
| Toothpowder composition prepared in Example 8 | 130.1 |
| Toothpowder composition prepared in Example 9 | 129.8 |
| Toothpowder composition prepared in Example 10 | 131.2 |
| Toothpowder composition prepared in Example 11 | 130.4 |
| Toothpowder composition prepared in Example 12 | 129.5 |
| Toothpowder composition prepared in Example 13 | 128.0 |
| Toothpowder composition prepared in Example 14 | 126.7 |
| Toothpowder composition prepared in Example 15 | 125.9 |
| Toothpowder composition prepared in Example 16 | 128.2 |
| Toothpowder composition prepared in Comparative Example 1 | 105.5 |
| Toothpowder composition prepared in Comparative Example 2 | 110.7 |
| Control 1 | 102.2 |
| Control 2 | 105.8 |

From the above results shown in Table 5, it was found that the toothpowder compositions in the inventive examples exhibit mostly excellent tooth whitening effects, compared to the toothpowder compositions in comparative examples as well as controls. Especially, the test results of the compositions obtained in examples and comparative examples demonstrated that wheat flour and bamboo salt used as the major ingredients used in embodiments of the present invention significantly influenced to the whitening effects.

From results compared between the inventive examples, it can be seen that the whitening effects are varied according to existence of individual materials and contents thereof. More particularly, it was determined that burnt alum and pine resin as well as wheat flour and bamboo salt have influenced to the whitening effects. From the foregoing experimental results, it can be understood that the methods for preparation of the toothpowder composition according to Example 1 and Examples 7 to 16 show the most optimal whitening effects.

Experimental Example 3

Determination of Tooth Whitening Effects of Human

1. Measurement Procedure

In order to determine real whitening effects of the toothpowder compositions prepared according to Example 1 and Examples 7 to 16, which show relatively favorable whitening effects in the foregoing Experimental Example 2, these compositions were directly applied to some participants over three months and the whitening effects were measured. Also, the toothpowder compositions prepared in Comparative Examples 1 and 2 and the controls, that is, commercial available toothpastes such as 'Song-yeom chi yak' (referring to a pine salt toothpaste, manufactured by Amore Pacific Corp.; Control 1) and 'Juk-yeom chi yak' (referring to a bamboo salt toothpaste, manufactured by LG Household & Health Care Ltd.; Control 2) were used for purposes of comparing tooth whitening effects thereof with embodiments of the present invention.

150 healthy participants with relatively yellowish teeth were selected and first underwent color measurement of the teeth using a color meter (manufactured by Trubyte Bioform). After dividing the participants into 15 groups with 10 persons per group, who have substantially the same mean value of the measured color, the inventive toothpowder composition was provided to each of the participants. For determination of an increase in lightness of the tooth, among 24 types standards for lightness in the color meter of Trubyte Bioform, sensibly distinguishable 10 types standards were selected. For each of these standards, a lightness value was counted in the range of the minimum of 1 to the maximum of 10. Before using the toothpowder composition for test, the lightness value of teeth for each group was evaluated down to the first decimal place based on the above standards. Following this, the lightness value of teeth of the same group after tooth brushing for 3 months was evaluated. An increase rate of a mean lightness value to the lightness value before test was calculated.

2. Test Results

TABLE 6

Tooth whitening effects - increase rate of lightness

| | Mean lightness value (before test) | Mean lightness value (after using 3 months) | Increase rate of lightness (%) |
|---|---|---|---|
| Toothpowder composition prepared in Example 1 | 3.4 | 5.9 | 73.5 |
| Toothpowder composition prepared in Example 7 | 3.4 | 5.4 | 58.8 |
| Toothpowder composition prepared in Example 8 | 3.4 | 5.5 | 61.8 |
| Toothpowder composition prepared in Example 9 | 3.5 | 5.4 | 54.3 |
| Toothpowder composition prepared in Example 10 | 3.5 | 5.5 | 57.1 |

TABLE 6-continued

Tooth whitening effects - increase rate of lightness

| | Mean lightness value (before test) | Mean lightness value (after using 3 months) | Increase rate of lightness (%) |
|---|---|---|---|
| Toothpowder composition prepared in Example 11 | 3.5 | 5.4 | 54.3 |
| Toothpowder composition prepared in Example 12 | 3.6 | 5.5 | 52.8 |
| Toothpowder composition prepared in Example 13 | 3.6 | 5.4 | 50.0 |
| Toothpowder composition prepared in Example 14 | 3.6 | 5.3 | 47.2 |
| Toothpowder composition prepared in Example 15 | 3.7 | 5.3 | 43.2 |
| Toothpowder composition prepared in Example 16 | 3.7 | 5.2 | 40.5 |
| Toothpowder composition prepared in Comparative Example 1 | 3.7 | 4.4 | 18.9 |
| Toothpowder composition prepared in Comparative Example 2 | 3.8 | 4.1 | 7.9 |
| Control 1 | 3.8 | 4.7 | 23.7 |
| Control 2 | 3.8 | 4.3 | 13.2 |

As shown in the Table 6, it was found that the toothpowder compositions in the inventive examples exhibit mostly high increase rate of lightness, compared to the toothpowder compositions in comparative examples as well as controls.

Also, from results compared between the inventive examples, it can be seen that improvement in lightness of tooth is varied according to existence of individual materials and contents thereof. More particularly, it was determined that burnt alum and pine resin as well as wheat flour and bamboo salt powder have influenced to increase in lightness values. Consequently, the foregoing experimental results demonstrated that the toothpowder composition according to embodiments of the present invention may considerably contribute improvement in tooth whitening effect as a beneficial performance of toothpaste products.

Experimental Example 4

Sterilization Experiment

1. Measurement Procedure

In order to determine sterilization effects of the toothpowder compositions prepared in the inventive examples, the following measurement was performed. Also, the toothpowder compositions prepared in Comparative Examples 1 and 2 and the controls, that is, commercial available toothpastes such as 'Song-yeom chi yak' (referring to a pine salt toothpaste, manufactured by Amore Pacific Corp.; Control 1) and 'Juk-yeom chi yak' (referring to a bamboo salt toothpaste, manufactured by LG Household & Health Care Ltd.; Control 2) were used for purposes of comparing sterilization effects thereof with embodiments of the present invention.

The inventive toothpowder composition was added to a BHI broth in a concentration of 0.02 to 0.5%, and then, a sample containing streptococcus mutant (ATCC 27607, 6735) as a tester strain, which causes mouth diseases such as tooth cavities, was inoculated on the broth and incubated at 37° C. for 48 hours. Then, each of the cultured media was spread out on an agar plate with a smear loop and incubated again for 48 hours, followed by defining a minimum inhibiting concentration (MIC) at which the tester strain grows no more. Cultured results are shown in the following Table 7.

2. Test Results

TABLE 7

Measured results of sterilization effects (MIC) (μg/ml)

|  | MIC |
|---|---|
| Toothpowder composition prepared in Example 1 | 0.080 |
| Toothpowder composition prepared in Example 2 | 0.078 |
| Toothpowder composition prepared in Example 3 | 0.075 |
| Toothpowder composition prepared in Example 4 | 0.078 |
| Toothpowder composition prepared in Example 5 | 0.077 |
| Toothpowder composition prepared in Example 6 | 0.080 |
| Toothpowder composition prepared in Example 7 | 0.085 |
| Toothpowder composition prepared in Example 8 | 0.088 |
| Toothpowder composition prepared in Example 9 | 0.082 |
| Toothpowder composition prepared in Example 10 | 0.084 |
| Toothpowder composition prepared in Example 11 | 0.088 |
| Toothpowder composition prepared in Example 12 | 0.087 |
| Toothpowder composition prepared in Example 13 | 0.089 |
| Toothpowder composition prepared in Example 14 | 0.084 |
| Toothpowder composition prepared in Example 15 | 0.085 |
| Toothpowder composition prepared in Example 16 | 0.088 |
| Toothpowder composition prepared in Comparative Example 1 | 0.090 |
| Toothpowder composition prepared in Comparative Example 2 | 0.154 |
| Control 1 | 0.088 |
| Control 2 | 0.085 |

As shown in the Table 7, it was found that the toothpowder compositions in the inventive examples exhibit mostly excellent sterilization effects, compared to the toothpowder compositions in comparative examples. Especially, it was determined that bamboo salt powder is the more important constitutional ingredient than wheat flour in terms of sterilization effects. In addition, the sterilization effects of the inventive toothpowder compositions were not too inferior below those of the controls. Consequently, the foregoing experimental results demonstrated that the toothpowder composition according to embodiments of the present invention exhibits favorable sterilization effects as well as tooth whitening effects.

Experimental Example 5

Evaluation of Tooth Abrasiveness

1. Measurement Procedure

In order to determine tooth abrasiveness of each of the toothpowder compositions according to embodiments of the present invention, the following experiment was performed. Also, the toothpowder compositions prepared in Comparative Examples 1 and 2 and the controls, that is, commercial available toothpastes such as 'Song-yeom chi yak' (referring to a pine salt toothpaste, manufactured by Amore Pacific Corp.; Control 1) and 'Juk-yeom chi yak' (referring to a bamboo salt toothpaste, manufactured by LG Household & Health Care Ltd.; Control 2) were used for purposes of comparing abrasiveness thereof with embodiments of the present invention.

More particularly, using a sanding cloth and 1 μm diamond paste, a bottom face of a processed tooth specimen was polished. Before wearing, a thickness of the tooth specimen was measured using pioneer calipers. Then, the specimen was attached to a test jig using an adhesive and a load of 500 g was applied thereto. A 200 mm disc with a polishing fabric made of soft suede was placed on a typical polisher and a diluted solution containing the toothpowder and water in the ratio of 50:50 was poured on the suede fabric with an amount of 10 ml at an interval of 10 minutes while rotating the disc. Wearing was performed at 100 rpm for 5 hours and, after the wearing, a thickness of the specimen was measured.

2. Test Results

TABLE 8

Evaluation of tooth abrasiveness

|  | Before evaluation (mm) | After evaluation (mm) | Decrease in thickness (μm) | Change of surface condition |
|---|---|---|---|---|
| Toothpowder composition prepared in Example 1 | 5.00 | 4.94 | 60 | No change |
| Toothpowder composition prepared in Example 2 | 5.00 | 5.00 | 0 | No change |
| Toothpowder composition prepared in Example 3 | 5.00 | 5.00 | 0 | No change |
| Toothpowder composition prepared in Example 4 | 5.00 | 5.00 | 0 | No change |
| Toothpowder composition prepared in Example 5 | 5.00 | 4.91 | 90 | No change |
| Toothpowder composition prepared in Example 6 | 5.00 | 5.00 | 0 | No change |
| Toothpowder composition prepared in Example 7 | 5.00 | 5.00 | 0 | No change |
| Toothpowder composition prepared in Example 8 | 5.00 | 4.95 | 50 | No change |
| Toothpowder composition prepared in Example 9 | 5.00 | 4.97 | 30 | No change |
| Toothpowder composition prepared in Example 10 | 5.00 | 4.99 | 10 | No change |
| Toothpowder composition prepared in Example 11 | 5.00 | 4.96 | 40 | No change |
| Toothpowder composition prepared in Example 12 | 5.00 | 4.97 | 30 | No change |
| Toothpowder composition prepared in Example 13 | 5.00 | 4.96 | 40 | No change |
| Toothpowder composition prepared in Example 14 | 5.00 | 4.99 | 10 | No change |
| Toothpowder composition prepared in Example 15 | 5.00 | 5.00 | 0 | No change |
| Toothpowder composition prepared in Example 16 | 5.00 | 4.98 | 20 | No change |
| Toothpowder composition prepared in Comparative Example 1 | 5.00 | 4.93 | 70 | No change |
| Toothpowder composition prepared in Comparative Example 2 | 5.00 | 5.00 | 0 | No change |
| Control 1 | 5.00 | 4.54 | 460 | Slight change |

TABLE 8-continued

Evaluation of tooth abrasiveness

|  | Before evaluation (mm) | After evaluation (mm) | Decrease in thickness (μm) | Change of surface condition |
|---|---|---|---|---|
| Control 2 | 5.00 | 4.73 | 270 | Slight change |

As shown in the Table 8, it was found that the toothpowder compositions in the inventive examples exhibit reduced abrasiveness, compared to the toothpowder compositions in comparative examples as well as the controls. Especially, it was found that such abrasiveness depends on burnt alum as a constitutional ingredient of the toothpowder composition according to embodiments of the present invention.

Consequently, the foregoing experimental results demonstrated that the toothpowder composition according to embodiments of the present invention may reduce abrasion of teeth while having tooth whitening effects and sterilization effects.

As is apparent from the above detailed description, the toothpowder composition and the tablet type toothpaste according to embodiments of the present invention have noticeably superior performances over conventional toothpaste products, as shown in test results for whitening, cleaning and sterilization effects, and abrasiveness. Especially, the inventive composition and tablet type toothpaste exhibit excellent effects in oral hygiene and tooth whitening, thereby being effectively used in industrial applications for manufacturing healthcare/hygienic products.

While the present invention has been described with reference to embodiments, it will be understood by those skilled in the art that various modifications and variations may be made therein without departing from the scope of the present invention as defined by the appended claims.

What is claimed is:

1. A toothpowder composition comprising: wheat flour, bamboo salt, burnt alum, pine resin, *Nelumbo Nucifera Gaertner*, *Asiasarum*, *Cimicifuga heracleifolia*, *Angelica Dahurica*, *Platycodon Grandiflorus* and *Flammulina velutipes*.

2. The toothpowder composition according to claim 1, wherein the wheat flour is in an amount from about 20 to 40 wt % of the total weight of the composition, and wherein the bamboo salt is in an amount from about 20 to about 40 wt. % of the total weight of the composition.

3. The toothpowder composition according to claim 1, wherein the burnt alum is in an amount from about 5 to about 15 wt. % of the total weight of the composition, and wherein the pine resin is in an amount from about 5 to about 15 wt. % of the total weight of the composition.

4. The toothpowder composition according to claim 1, wherein the burnt alum is in an amount from about 5 to about 15 wt. %, wherein the pine resin is in an amount from about 5 to about 15 wt. %, wherein the *Nelumbo Nucifera Gaertner* is in an amount from about 2 to about 6 wt. %, wherein the *Asiasarum* is in an amount from about 2 to about 6 wt. %, wherein the *Cimicifuga heracleifolia* is in an amount from about 2 to about 6 wt. %, wherein the *Angelica Dahurica* is in an amount from about 2 to about 6 wt. %, wherein the *Platycodon Grandiflorus* is in an amount from about 1 to about 3 wt. %, wherein the *Flammulina velutipes* is in an amount from about 1 to about 3 wt. %, wherein the composition further comprises the one or more substances in powder form, and wherein the foregoing amount is relative to the total weight of the composition.

5. A method of manufacturing a toothpowder composition comprising:
providing powder substances comprising bamboo salt, burnt alum, pine resin, *Nelumbo Nucifera Gaertner*, *Asiasarum*, *Cimicifuga heracleifolia*, *Angelica Dahurica*, *Platycodon Grandiflorus* and *Flammulina velutipes*; and
mixing the powder substances with wheat flour to provide the toothpowder composition of claim 1.

6. The method according to claim 5, wherein providing the powder substances comprises:
providing bamboo salt;
heating the bamboo salt; and
pulverizing the once-heated bamboo salt into bamboo salt powder.

7. The method according to claim 5, wherein providing the powder substances comprises:
providing burnt alum or pine resin;
heating the burnt alum or pine resin; and
pulverizing the once-heated burnt alum or pine resin into powder.

8. The method according to claim 5, wherein providing the powder substances comprises:
providing substances comprising *Nelumbo Nucifera Gaertner*, *Asiasarum*, *Cimicifuga heracleifolia*, *Angelica Dahurica*, *Platycodon Grandiflorus* and *Flammulina velutipes*;
drying the substances under a shade; and
pulverizing the dried substances into powders.

9. The method according to claim 5, wherein an amount of the bamboo salt has a particle size from about 0.1 to about 150 μm,
wherein an amount of the burnt alum has a particle size from about 0.1 to about 3 μm,
wherein an amount of the pine resin has a particle size from about 0.1 to about 50 μm,
wherein an amount of the *Nelumbo Nucifera Gaertner* has a particle size from about 0.1 to about 55 μm,
wherein an amount of the *Asiasarum* has a particle size from about 0.1 to about 10 μm,
wherein an amount of the *Cimicifuga heracleifolia* has a particle size from about 0.1 to about 10 μm,
wherein an amount of the *Angelica Dahurica* has a particle size from about 0.1 to about 25 μm,
wherein an amount of the *Platycodon Grandiflorus* has a particle size from about 0.1 to about 70 μm,
wherein an amount of the *Flammulina velutipes* has a particle size from about 0.1 to about 80 μm, and
wherein an amount of the wheat flour has a particle size from about 0.1 to about 25 μm.

10. The method according to claim 6, wherein providing the powder substances comprises screening the bamboo salt powder using a sieve having 150 to 180 mesh.

11. The method according to claim 5, wherein providing the powder substances comprises screening the powder substances using a sieve having 150 to 180 mesh.

12. A method of manufacturing a tablet toothpaste comprising:
forming the toothpowder composition of claim 1 into a tablet and applying a coating solution to the tablet.

13. The method according to claim 12, wherein the forming comprises:
mixing the toothpowder composition with water to provide a water-added mixture;

shaping the water-added mixture into the tablet shape; and drying the tablet.

14. The method according to claim 12, wherein the coating solution comprises at least one selected from the group consisting of hydroxypropyl methylcellulose and palatinose.

* * * * *